(12) United States Patent
Wang et al.

(10) Patent No.: US 7,176,036 B2
(45) Date of Patent: *Feb. 13, 2007

(54) ELECTROACTIVE MICROSPHERES AND METHODS

(75) Inventors: Joseph Wang, Las Cruces, NM (US); Ronen Polsky, Las Cruces, NM (US); Kathryn L. Turner, Fishers, IN (US)

(73) Assignee: Arrowhead Center, Inc., Las Cruces, NM (US)

( * ) Notice: Subject to any disclaimer, the term of this patent is extended or adjusted under 35 U.S.C. 154(b) by 94 days.

This patent is subject to a terminal disclaimer.

(21) Appl. No.: 10/666,412

(22) Filed: Sep. 18, 2003

(65) Prior Publication Data

US 2004/0058389 A1    Mar. 25, 2004

Related U.S. Application Data

(60) Provisional application No. 60/412,246, filed on Sep. 20, 2002.

(51) Int. Cl.
*G01N 33/551* (2006.01)
*C10G 32/00* (2006.01)

(52) U.S. Cl. ...................... 436/524; 436/518; 436/525; 436/526; 436/164; 436/169; 436/172; 436/528; 436/530; 436/533; 436/534; 436/536; 436/538; 436/541; 436/805; 436/801; 436/815; 436/810; 435/281.2; 435/287.2; 204/1.93; 204/286.1; 204/288; 204/403.01

(58) Field of Classification Search ................ 436/518, 436/524, 526, 525, 164, 169, 172, 528, 530, 436/533, 534, 536, 538, 541, 805, 801, 810, 436/815; 435/281.2, 287.2; 204/193, 286.1, 204/288, 403.01
See application file for complete search history.

(56) References Cited

U.S. PATENT DOCUMENTS

| 4,205,952 | A | | 6/1980 | Cais |
| 4,233,144 | A | * | 11/1980 | Pace et al. ................... 436/544 |
| 4,663,277 | A | * | 5/1987 | Wang ............................. 435/5 |
| 5,512,659 | A | | 4/1996 | Ullman et al. |
| 5,753,517 | A | * | 5/1998 | Brooks et al. ............... 436/514 |
| 5,753,519 | A | | 5/1998 | Durst et al. |
| 5,756,362 | A | | 5/1998 | Durst et al. |
| 5,789,154 | A | | 8/1998 | Durst et al. |
| 5,942,388 | A | | 8/1999 | Willner et al. |

(Continued)

OTHER PUBLICATIONS

Susan R. Mikkelsen, "Electrochemical Biosensors for DNA Sequence Detection", *Electroanalysis*, 1996, 8, No. 1.

(Continued)

*Primary Examiner*—Long V. Le
*Assistant Examiner*—Pensee T. Do
(74) *Attorney, Agent, or Firm*—Stephen A. Slusher; Janeen Vilven; Peacock Myers, P.C.

(57) ABSTRACT

Methods and devices for electrochemical detection of a specific binding pair member utilizing a microsphere with an incorporated electroactive marker, wherein a member of the specific binding pair to be detected is bound, directly or through one or more intermediates, to the microsphere. Multiple specific binding pair members may be detected by use of electrochemically distinguishable electroactive markers. Microspheres with incorporated electroactive markers may include one or more functional groups for binding members of specific binding pairs, and are preferably insoluble in aqueous solvents but soluble in selected organic solvents.

23 Claims, 6 Drawing Sheets

U.S. PATENT DOCUMENTS

| | | | |
|---|---|---|---|
| 5,958,791 | A | 9/1999 | Roberts et al. |
| 5,981,180 | A | 11/1999 | Chandler et al. |
| 6,086,748 | A | 7/2000 | Durst et al. |
| 6,087,748 | A | 7/2000 | Donner |
| 6,096,825 | A * | 8/2000 | Garnier .................... 525/54.1 |
| 6,159,745 | A | 12/2000 | Roberts et al. |
| 6,221,586 | B1 | 4/2001 | Barton |
| 6,248,596 | B1 | 6/2001 | Durst et al. |
| 6,264,825 | B1 | 7/2001 | Blackburn et al. |
| 6,274,323 | B1 * | 8/2001 | Bruchez et al. ............... 435/6 |
| 6,277,304 | B1 * | 8/2001 | Wei et al. ................... 252/500 |
| 6,287,765 | B1 | 9/2001 | Cubicciotti |
| 6,291,188 | B1 | 9/2001 | Meade et al. |
| 6,355,224 | B1 * | 3/2002 | Shastri et al. ............... 424/9.3 |
| 6,358,752 | B1 | 3/2002 | Durst et al. |
| 6,368,800 | B1 | 4/2002 | Smith et al. |
| 6,387,624 | B1 | 5/2002 | Fu et al. |
| 6,387,625 | B1 | 5/2002 | Eckhardt et al. |
| 6,461,820 | B1 | 10/2002 | Barton et al. |
| 6,485,983 | B1 * | 11/2002 | Lu et al. ..................... 436/514 |
| 6,506,564 | B1 | 1/2003 | Mirkin et al. |
| 6,528,266 | B2 | 3/2003 | Meade |
| 6,541,617 | B1 * | 4/2003 | Bamdad et al. ............ 536/23.1 |
| 6,548,264 | B1 * | 4/2003 | Tan et al. ................... 435/7.21 |
| 6,548,311 | B1 * | 4/2003 | Knoll ......................... 436/524 |
| 6,610,491 | B2 | 8/2003 | Mirkin et al. |
| 6,630,307 | B2 * | 10/2003 | Bruchez et al. ............... 435/6 |
| 6,680,211 | B2 * | 1/2004 | Barbera-Guillem et al. 436/533 |
| 6,682,647 | B1 | 1/2004 | Wang |
| 6,713,308 | B1 * | 3/2004 | Lu et al. ..................... 436/514 |
| 2002/0048822 | A1 | 4/2002 | Rittenburg et al. |
| 2002/0155507 | A1 | 10/2002 | Bruchez et al. |
| 2002/0164271 | A1 | 11/2002 | Ho |
| 2002/0164611 | A1 | 11/2002 | Bamdad et al. |
| 2002/0187501 | A1 | 12/2002 | Huong et al. |
| 2003/0059955 | A1 * | 3/2003 | Bamdad ..................... 436/524 |
| 2003/0077625 | A1 | 4/2003 | Hutchison |
| 2003/0082237 | A1 | 5/2003 | Cha et al. |
| 2003/0104386 | A1 | 6/2003 | Kuhr et al. |
| 2003/0143581 | A1 | 7/2003 | Franzen et al. |
| 2003/0232354 | A1 | 12/2003 | Yu et al. |

OTHER PUBLICATIONS

Joseph Wang, "Towards Genoelectronics: Electrochemical Biosensing of DNA Hybridization", *Chem. Eur. J.* 1999, 5, No. 6.

Joseph Wang, et al., "Metal Nanoparticle-Based Electrochemical Stripping Potentiometric Detection of DNA Hybridization", *Analytical Chemistry*.

Joseph Wang, *Analytical Electrochemistry*, VCH Publishers, Inc., New York, 1994.

E. Palacek,, M. Fojta, *Analytical Chemistry*, 2001, 73, 75A.

Harlow and Lane, *Antibodies: A Laboratory Manual*, Cold Spring Harbor Laboratory, 1988, TEXTBOOK.

Cao, Yunwei C., et al., "Nanoparticles with Raman Spectroscopic Fingerprints for DNA and RNA Detection", *Science*, vol. 297, (Aug. 30, 2002), 1536-1540.

Chen, Yongfen, et al., "Luminescent CdSe Quantum Dot Doped Stabilized Micelles", *Nano Letters, Ameri Chemical Society*, vol. 2, No. 11, (2002), 128801392.

Du, H. , et al., "Synthesis, Characterization, and Nonlinear Optical Properties of Hybridized CdS—Polystyrene Nanocomposites", *Chem. Mater.*, vol. 14, (2002),4473-4479.

Ferguson, Jane A., et al., "High-Density Fiber-Optic DNA Random Microsphere Array", *Anal. Chem*, vol. 72, (2002),5618-5624.

Han, Mingyong, et al., "Quantum-Dot-Tagged Microbeads for Multiplexed Optical Coding of Biomolecules", *Nature Biotechnology*, vol. 19, (Jul. 2001),631-635.

Martin, Charles R., "Template Synthesis of Electronically Conductive Polymer Nanostructures", *Acc. Chem. Res*, vol. 28, (1995),61-68.

Nicewarner-Pena, Sheila R., et al., "Submicrometer Metallic Barcodes", *Science*, vol. 294,(Oct. 5, 2001),137-141.

Rosenthal, Sandra J., "Bar-Coding Biomolecules with Fluorescent Nanocrystals", *Nature Biotechnology*, vol. 19, (Jul. 2001),621-622.

Taton, T. A., et al., "Two-Color Labeling of Oligonucleotide Arrays via Size-Selective Scattering of Nanoparticle Probes", *J. Am. Chem. Soc*, 123, (2001),5164-5165.

Trau, Dieter, et al., "Nanoencapsulated Microcrystalline Particles for Superamplified Biochemical Assays", *Anal. Chem*, vol. 74, (2002),5480-5486.

Wang, Joseph , et al., "Electroactive Beads for Ultrasensitive DNA Detection", *Amer. Chem*, vol. 75, (2002).

Wang, Joseph , et al., "Electrochemical Detection of DNA Hubridization Based on Carbon-Nanotubes loaded wih CdS Tags", *Electrochemistry Communications*, vol. 5, (2003), 1000-1004.

Wang, Joseph , "Electrochemical Nucleic Acid Biosensors", *Analytica Chimica Acta*, vol. 469, (2002),36-71.

Wang, Joseph , et al., "Encoded Beads for Electrochemical Identification", *Anal. Chem.* vol. 75, (2003),4667-4671.

Wang, Joseph , et al., "Indium Microrod Tags for Electrochemical Detection of DNA Hybridization", *Anal. Chem*, vol. 75, (2003),6218-6222.

Wang, Joseph , "Nanoparticle-Based Electrochemical DNA Detection", *Analytica Chimica Acta*, vol. 500, (2003),247-257.

* cited by examiner

SEQUENCE LISTING

<160> NUMBER OF SEQ ID NOS: 9

<210> SEQ ID NO 1
<211> LENGTH: 28
<212> TYPE: DNA
<213> ORGANISM: Artificial
<220> FEATURE:
<223> OTHER INFORMATION: Synthetic probe sequence for derived E908X mutation BRCA1 sequence

<400> SEQUENCE: 1
gtattagctt ttcttgataa aatcctca                          28

<210> SEQ ID NO 2
<211> LENGTH: 28
<212> TYPE: DNA
<213> ORGANISM: Artificial
<220> FEATURE:
<223> OTHER INFORMATION: Derived E908X mutation BRCA1 sequence

<400> SEQUENCE: 2
gtattagctt gaggatttta tcaagaaa                          28

<210> SEQ ID NO 3
<211> LENGTH: 28
<212> TYPE: DNA
<213> ORGANISM: Artificial
<220> FEATURE:
<223> OTHER INFORMATION: Synthetic non-complementary target sequence

<400> SEQUENCE: 3
gtattagctg aacaaaagga agaaaatc                          28

<210> SEQ ID NO 4
<211> LENGTH: 20
<212> TYPE: DNA
<213> ORGANISM: Artificial
<220> FEATURE:
<223> OTHER INFORMATION: Synthetic biotinylated probe sequence

<400> SEQUENCE: 4
gggtttatga aaaacacttt                                    20

<210> SEQ ID NO 5
<211> LENGTH: 20
<212> TYPE: DNA
<213> ORGANISM: Artificial
<220> FEATURE:
<223> OTHER INFORMATION: Synthetic biotinylated probe sequence

<400> SEQUENCE: 5
acactgggtg ggctagggaa                                    20

<210> SEQ ID NO 6
<211> LENGTH: 20
<212> TYPE: DNA
<213> ORGANISM: Artificial
<220> FEATURE:
<223> OTHER INFORMATION: Synthetic biotinylated probe sequence

<400> SEQUENCE: 6
gacctagtcc ttccaacagc                                    20

<210> SEQ ID NO 7

-continued

```
<211> LENGTH: 20
<212> TYPE: DNA
<213> ORGANISM: Artificial
<220> FEATURE:
<223> OTHER INFORMATION: Synthetic biotinylated probe sequence

<400> SEQUENCE: 7
caaaacgtat tttgtacaat                                              20

<210> SEQ ID NO 8
<211> LENGTH: 60
<212> TYPE: DNA
<213> ORGANISM: Artificial
<220> FEATURE:
<223> OTHER INFORMATION: Synthetic target sequence

<400> SEQUENCE: 8
aaagtgtttt tcataaaccc attatccagg actgtttata gctgttggaa ggactaggtc  60

<210> SEQ ID NO 9
<211> LENGTH: 60
<212> TYPE: DNA
<213> ORGANISM: Artificial
<220> FEATURE:
<223> OTHER INFORMATION: Synthetic target sequence

<400> SEQUENCE: 9
ttccctagcc cacccagtgt gcaagggcag tgaagacttg attgtacaaa atacgttttg  60
```

ELECTROACTIVE MICROSPHERES AND METHODS

CROSS-REFERENCE TO RELATED APPLICATION

This application claims the benefit of the filing of U.S. Provisional Patent Application Ser. No. 60/412,246, entitled "Encapsulated Electroactive Marker Systems and Methods", filed on Sep. 20, 2002, and the specification thereof is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant Number CHE 0209707 awarded by the National Science Foundation and Award No. DAMD17-00-1-0366 awarded by U.S. Army Medical Research.

BACKGROUND OF THE INVENTION

1. Field of the Invention (Technical Field)

The present invention relates to devices, systems and methods for electrochemical detection of specific binding pair interactions utilizing microspheres with incorporated electroactive markers, wherein one member of the specific binding pair is bound, directly or through one or more intermediates, to the surface of the microsphere.

2. Description of Related Art

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

Detection of analytes, and particularly detection of analytes wherein the analyte is a member of a specific binding pair, is well known in the art. A wide variety of bioassays are known which use a number of different reporting systems, such as fluorescent probes, radioactive markers and the like.

One specific binding pair that can be detected is DNA hybridization, used for diagnosis and treatment of genetic diseases, for the detection of infectious agents, for reliable forensic analysis and other purposes. DNA sensing applications require high sensitivity through amplified transduction of the oligonucleotide interaction. Electrical detection of DNA hybridization has shown great promise for this purpose and has thus been the subject of intense research activity. (Mikkelsen, S. R. *Electroanalysis,* 1996, 8, 15; Wang, *J. Chem. Eur. J.* 1999, 5, 1681; Palecek, E.; Fojta, M. *Anal. Chem.* 2001, 73, 75A; see also U.S. Pat. No. 6,387,625). Such electronic transduction is commonly accomplished by using intercalating electroactive indicators (that associate with the surface hybrid), through enzyme-amplified recognition, by monitoring the intrinsic redox activity of DNA, or through redox tags covalently bound to single-stranded DNA oligomers. In particular, the use of ferrocene-oligonucleotide conjugates has been shown extremely useful for monitoring DNA and RNA down to the femtomol level. However, the sensitivity of such systems has suffered because of lack of an adequate reporter or amplification system for detecting small quantities of analytes.

U.S. Pat. No. 6,087,748 discloses liposomes encapsulating an electroactive marker in a specific test device with a contact portion, an electrochemical measurement portion, and a liposome lysing portion with a liposome lysing agent. However, this approach is limited by the inherent fragility of phospholipid bilayer constructs and the limited size and carrying capacity of liposomes, as well as the permeability of liposome membranes.

There remains a need for a method of employing electrochemical detection of analytes, such as members of specific binding pairs, which provides a reporting and amplification system, and further optionally provides a method for detection of extremely low levels of analytes.

BRIEF SUMMARY OF THE INVENTION

The invention provides a method of analyzing a sample for the presence of a member of a specific binding pair. In the method, there is provided a microsphere having an incorporated electroactive marker, with the microsphere selected for by formation of a specific binding pair complex, and thereafter an electrochemical test for the electroactive marker is employed.

The methods further provide for analyzing a sample for the presence of two or more analytes. In this method, a first microsphere having an incorporated first electroactive marker and a second microsphere having an incorporated second electroactive marker electrochemically distinguishable from the first electroactive marker are provided. A first binding pair member specific to a first analyte is attached to the first microsphere, and a second binding pair member specific to a second analyte is attached to the second microsphere. Following incubation of the first microsphere and second microsphere in a solution including the sample to be analyzed, the first microsphere and second microsphere are selected for by formation of specific binding pair complexes. Thereafter electrochemical testing is employed to detect the presence or absence, and optionally to quantify, the first electroactive marker and the second electroactive marker. In the practice of the invention, up to at least about six different electroactive markers may be so employed.

In the methods of the invention, the microsphere is preferably a polymeric microsphere that is insoluble in an aqueous solution, such as a polystyrene-based microsphere. The electroactive marker can be incorporated into the body of the microsphere, such as by incubation of a polymeric microsphere in an organic solvent including the electroactive marker. Alternatively, the electroactive marker can be incorporated by association with the surface of microsphere, such as binding by means of an avidin-biotin complex.

In the methods of the invention, the selecting step can include a first member of a specific binding pair attached to a microsphere and a second member of the specific binding pair attached to a substrate. The first member of the specific binding pair attached to the microsphere can include a covalent bond with a functional group on the surface of the microsphere. In one embodiment, the substrate includes a magnetic particle. The selecting step can also include incubation for sufficient time and under appropriate solvent and temperatures parameters to permit formation of a specific binding pairs.

Representative specific binding pair complexes that can be employed in the methods of the invention include, but are not limited to, antigen/antibody, enzyme/substrate, oligonucleotide/DNA, chelator/metal, enzyme/inhibitor, bacteria/ receptor, virus/receptor, hormone/receptor, DNA/RNA, RNA/RNA, and oligonucleotide/RNA complexes.

The methods can further include releasing the electroactive marker from the microsphere. One method of release includes solubilizing the microsphere. In the methods, the electroactive marker can include a metallocene, a nanoparticle or a metal.

In the methods, electrochemically testing includes measurement of one or more electrical quantities in relationship to one or more chemical parameters. Measured electrical quantities can include current, potential or charge. Thus measurement of one or more electrical quantities can include chronopotentiometric detection, stripping potentiometry, stripping chronopotentiometry, anodic stripping voltammetry, cathodic stripping voltammetry, or adsorptive stripping voltammetry.

The invention further provides a microsphere for electrochemical detection of a member of a specific binding pair, wherein the microsphere is polymeric microsphere having an organic solvent soluble hydrophobic electroactive marker incorporated into the body of the microsphere and at least one functional group on the surface of the microsphere. In a preferred embodiment, the soluble hydrophobic electroactive marker is non-magnetic. Thus the soluble hydrophobic electroactive marker may be a metallocene, such as ferrocene or ferrocenecarboxaldehyde. The at least one functional group on the surface of the microsphere may include a sulfate surface group, aldehyde group, aliphatic amine group, amide group, aromatic amine group, carboxylic acid group, chloromethyl group, epoxy group, hydrazide group, hydroxyl group, sulfonate group or tosyl group. In a preferred embodiment, the polymeric microsphere is a polystyrene-based microsphere, preferably with a diameter between about 0.01 µm and about 100.0 µm, more preferably between about 0.3 µm and about 20 µm.

A primary object of the present invention is to provide devices and methods for electrochemical detection of specific binding pair interaction utilizing a reporter system including electroactive markers incorporated into a microsphere.

Another object of the invention is to provide a method of electrochemical detection for use with microspheres wherein assay protocols and techniques used with other reporter systems, such as fluorescent microspheres, may readily be adapted to electrochemical detection.

Another object is to provide microspheres, preferably polymeric microspheres, with incorporated electroactive markers, preferably metallocene electroactive markers.

Yet another object is to provide a method for electrochemical detection of specific binding pair interactions, where one member of the pair is bound, directly or through one or more intermediates, to the exterior surface of a microsphere with incorporated electroactive markers.

A primary advantage of the present invention is that it provides a method for performing sandwich-specific binding pair interaction assays, including sandwich DNA hybridization assays, coupled with a reporter system including electrochemical detection of electroactive markers incorporated in a microsphere.

Another object of the present invention is that it provides devices and methods for electrochemical detection of very small quantities of analytes, as low as at least $5.1 \times 10^{-21}$ mol for DNA hybridization detection.

Another object of the present invention is to provide devices and methods which provide for incorporation of large quantities of electroactive markers within a single bead, up to at least about $5 \times 10^{11}$ molecules of electroactive markers per microsphere.

Another object is to provide for simultaneous electrochemical detection of multiple analytes, utilizing microspheres targeted to different analytes, with each different analyte microsphere having an electrochemically distinguishable electroactive marker.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
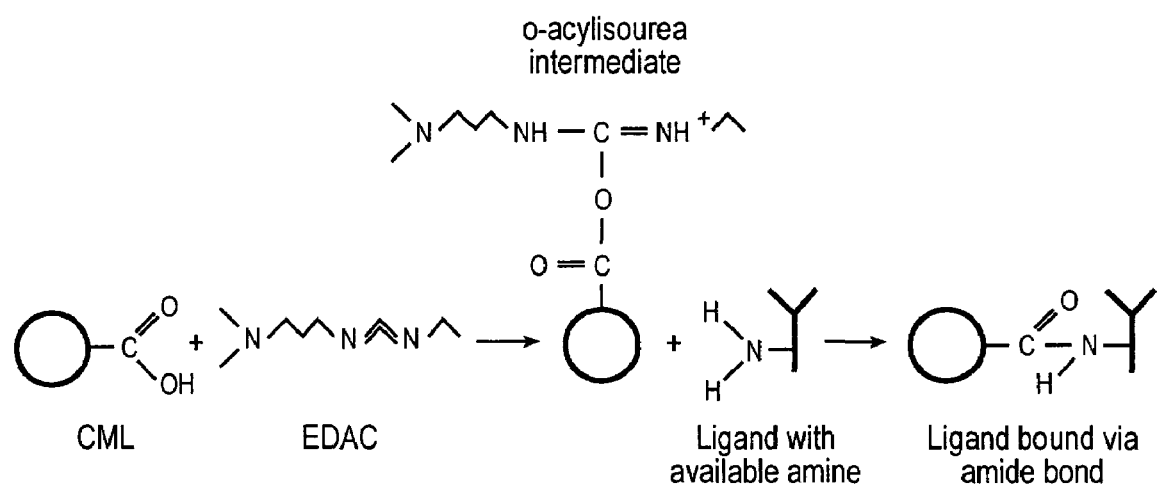
FIG. 1 graphically depicts one embodiment of the invention, wherein a microsphere containing the incorporated electroactive marker is covalently bonded to an analyte through one or more intermediates, such as an analyte with an available endogenous amine or derivatized with an amine, with capture by any means, such as sandwich DNA hybridization or an immunological reaction.

In one embodiment, the invention provides a soluble microsphere or microbead (the terms are used interchangeably) with an incorporated electroactive marker. The soluble microsphere with an electroactive marker can be employed in any assay or method wherein microspheres are conventionally employed, particularly to detect binding by a member of a specific binding pair. Such microbeads can include one or more functional surface groups, optionally one or more intermediate groups, and one or more binding groups, such as a member of a specific binding pair.

In another embodiment, the invention provides a method for detecting and optionally quantifying an analyte or target that is a member of a specific binding pair. In the practice of the invention, a soluble microsphere is provided with an incorporated electroactive marker. The probe is attached to the surface of the microsphere by any means known in the art, including adsorption, covalent coupling, or complexation with a receptor-specific compound or agent. The probe-coated microsphere is mixed and allowed to react with a complementary member of the binding pair, preferably wherein the complementary member of the binding pair is attached, by any means known in the art, to a separation means, such as a slide, tube, well of a plate, magnetic microsphere, dipstick or the like, wherein such separation means permits separation of probe-coated microspheres bound to a complementary member of the specific binding pair from probe-coated microspheres not bound to a complementary member of the specific binding pair. Thereafter the probe-coated microsphere is solubilized or partially solubilized, effecting release of the incorporated electroactive marker. The electroactive marker is then detected by electrochemical detection.

Before further disclosure of the scope and intent of the invention, the following terms are defined.

A "specific binding pair" is any pair, at least one of which is of biological origin or derivation, which binds or forms a complex with another molecule or molecular structure, and thus includes, but is not limited to, antigen/antibody, enzyme/substrate, oligonucleotide/DNA, chelator/metal, enzyme/inhibitor, bacteria/receptor, virus/receptor, hormone/receptor, DNA/RNA, RNA/RNA, and oligonucleotide/RNA pairs, as well as binding of any member of the foregoing pairs to any other member, and interaction, resulting in the formation of a complex, with any member of the foregoing pairs to any molecular structure, including but not limited to inorganic species. Binding pair members can further include mimics and analogs of specific binding pair members, such as peptide mimetics of the binding region of antibodies or peptides specific for an oligonucleotide, DNA or RNA. As used herein, the term "member of a binding pair" includes all biomolecules which can bind to one another such as nucleic acids, receptors, ligands, antibodies, antigens and carbohydrates. While the examples herein primarily relate to use of oligonucleotides, one of ordinary skill in the art could use these examples and the disclosure herein for use with other biomolecules. For example, immunological applications based on antigen-antibody interaction are well known in the art.

An "analyte" or "target" is a member of a binding pair to be detected, qualitated and/or quantified.

A "probe" is a member of a binding pair, complementary to the analyte or target.

An "electroactive marker" is any marker or substantive, including redox markers, that can be detected by electrochemical detection such as by oxidation or reduction processes. Electroactive markers thus include various metallocene compounds, which include a positively charged metal ion sandwiched between two negatively charged cyclopentadienyl anions. Particularly preferred are ferrocene compounds, such as ferrocene, ferrocenecarboxaldehyde (FCA) or dimethyl-ferrocene. Electroactive markers further include compounds such as phenoxazine compounds, various metal compounds such as ruthenium or osmium complexes, quinone compounds, ferricyanide, phenothiazine compounds, organic conducting salts and various derivatives of the forgoing. Other electroactive markers that can be employed include various nanoparticles, such as CdS, ZnS, PbS or the like, as well as semiconductor particles such as InAs and GaAs. Colloidal gold nanoparticles, as well as colloidal preparations of other metals, may similarly be employed. In general, any compound or substance that can be detected by electrochemical detection can be employed as an electroactive marker. In a preferred embodiment, the electroactive marker is water insoluble. It is preferable that the marker be hydrophobic, to prevent leaking of the marker into aqueous solutions. However, alternatively the microsphere may be sealed by appropriate means. However, electroactive markers that are water soluble may be employed by using a non-porous shell on the microsphere, a sealant or the like.

"Electrochemical detection" includes the measurement of one or more electrical quantities, such as current, potential or charge, in relationship to one or more chemical parameters. For the present invention, preferred methods of electrochemical detection are chronopotentiometric measurements. However, other methods and means of electrochemical detection can be employed herein, provided that such methods or means permit detection of the electroactive marker. For example, with nanoparticles such as CdS, ZnS, or PbS, stripping voltammetry is a preferred method of electrochemical detection.

A "microsphere" is a particle, preferably generally spherical in shape, though the structural and spatial configuration of the particle is not critical to the present invention. For example, the particles could be slivers, ellipsoids, cubes, or the like. The microsphere is selected from materials that may be solubilized in a non-aqueous solvent but are insoluble in an aqueous solvent, and which may have diffused or incorporated therein or thereon an electroactive marker. Microspheres thus may include, but are not limited to, synthetic polymers or plastics, polystyrene, polycarbonate and the like. A preferred microsphere is a polystyrene-based microsphere which includes polystyrene with one or more monomers, such as divinyl benzene or an acrylic acid. Particle sizes range from a diameter of approximately 0.01 μm to 100.0 µm or greater, and are desirably from between approximately 0.3 µm to 20 µm. Microspheres are sometimes called "beads".

In the practice of the invention, any form of electrode may be used for electrochemical detection. Thus, the electrodes can be any of a wide variety of carbonaceous electrodes, including but not limited to carbon paste electrodes, glassy carbon electrodes, bare carbon electrodes, carbon-fiber microelectrodes, reticulated carbon electrodes, and the like, or can be any other form of electrode, including generally any conductive material, including but not limited to thick-film electrodes and screen-printed carbon-ink electrodes. Both thin-layer and thick-layer electrodes may be employed in the practice of this invention. The electrode may be of any size; typically a glassy-carbon disk electrode will have a working surface diameter from about 1.0 to about 5.0 mm, a carbon-fiber microelectrode will be approximately 1 mm in length and approximately 7 µm in diameter, and so on. Thin-film and screen-printed thick-film electrode working surfaces may be any convenient size, such as from a width of about 1 mm to about 5 mm, and a length from about 1 mm to about 10 mm. Other conducting electrodes may be employed, including electrodes made from a metal, such as gold or iridium. In all embodiments, there may be provided a reference electrode and a counter electrode. The reference electrode may conveniently be an Ag/AgCl wire, and the counter electrode may conveniently be a platinum wire. However, the reference and counter electrodes may be made from any suitable material, and may be in any desired shape or configuration. The electrode may include any base material or substrate, including polymeric materials, ceramics and the like.

Analysis may be by any means of electrochemical analysis. In one embodiment, chronopotentiometric detection at a glassy-carbon transducer is employed using a potentiometric stripping unit. However, any of a variety of forms of electrochemical analysis may be employed, including stripping potentiometry, stripping chronopotentiometry, anodic stripping voltammetry, cathodic stripping voltammetry, and adsorptive stripping voltammetry. For stripping voltammetry, any of a variety of waveforms can be employed, including square wave stripping voltammetry, linear sweep stripping voltammetry, differential pulse cathodic stripping voltammetry, and square wave adsorptive stripping voltammetry. Electrodes, methods of detection and analysis, and the like are generally disclosed in *Analytical Electrochemistry* by Joseph Wang, VCH Publishers, Inc., New York, 1994, incorporated herein by reference.

In one embodiment, microspheres are made from polymeric materials. The electroactive marker is contained in a solution including an organic solvent that solubilizes the polymeric matrix. The solvent causes swelling of the polymer and opening of pores in the structure thereof, such that the electroactive marker diffuses into the polymer matrix and is entrapped when the solvent is removed from the microspheres, such as through evaporation or transfer to an aqueous phase. A wide range of different solvent systems are known in the art, such as for incorporating fluorescene markers in microspheres, and in general such solvents and methods may be employed to incorporate electroactive markers. The microspheres may be made, for example, from polymerized styrene or styrene/divinylbenzene monomers. The quantity of electroactive marker can be varied; up to at least approximately $5\times10^{11}$ molecules of a ferrocenecarboxaldehyde marker can be incorporated into a single approximately 10 µm microsphere. Any suitable solvent may be employed in loading or incorporating the electroactive marker into the microspheres; the selection of solvent is dependant in part on the polymeric material from which the microsphere is made, and such solvents are known in the art. In a preferred embodiment, the electroactive marker is also soluble in the selected solvent.

In a preferred embodiment, the electroactive marker is incorporated into the polymeric material, such as into the matrix thereof, and thus is dispersed throughout the volume of the microsphere. In this way, it is possible to incorporate a maximum quantity of electroactive marker per microsphere. However, it is also possible and contemplated to incorporate the electroactive marker by association with the surface of the microsphere, or alternatively to both incorporate electroactive marker into the body of the microsphere and to incorporate electroactive marker by association with the microsphere surface. For example, albumin-biotin labeled colloidal gold particles of an approximately 5 nm size, the colloidal gold particles constituting an electroactive marker, may be incorporated by association with streptavidin-coated polystyrene microspheres.

The analyte or target may be bound to the microsphere by any means known in the art. In one embodiment, simple hydrophobic adsorption is employed, such as to a hydrophobic particle, for example binding a protein onto polystyrene particles. In other embodiments one or more functional groups and/or linkers may be employed. Functional groups that may be introduced to the surface of a microsphere include sulfate ($-SO_4$) surface groups, aldehyde groups ($-CHO$), aliphatic amine groups ($-CH_2-NH_2$), amide groups ($-CONH_2$), aromatic amine groups($-\emptyset-NH_2$), carboxylic acid groups ($-COOH$),chloromethyl ($-CH_2-Cl$), epoxy groups

hydrazide groups ($-CONH-NH_2$), hydroxyl groups ($-OH$), sulfonate groups ($-SO_3$), tosyl groups

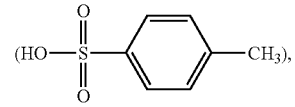

and the like. The functional groups permit a wide range of covalent coupling reactions for secure and stable attachment of peptides, proteins, oligonucleotides, and other biochemical ligands to the microsphere surfaces. Attachment may also be by means of, for example, binding using a protein A or protein G linker; binding using a streptavidin or avidin-biotin linker; or by employing any of a wide variety of other linkers, spacers and the like. As is known in the art, it is also possible to modify the analyte or target molecule, such as by means of biotinylation or amination, as a component of binding the analyte or target molecule to the microsphere. Any of a wide variety of buffers are used in various coupling reactions, including phosphate buffered saline, borate buffer, acetate buffer, citrate-phosphate buffer, carbonate-bicarbonate buffer, MES buffer and the like. It is also possible and contemplated to employ blockers coated onto the microspheres, which blockers may be any conventional blocker known in the art, including but not limited to bovine serum albumin, casein, pepticase, non-ionic surfactants, irrelevant immunoglobulins, fish skin gelatin, polyethylene glycol, non-cross-reactive sera and other commercial or proprietary blockers.

After the probe is bound to the microsphere containing incorporated electroactive markers, the microsphere may be employed in any assay system or method in which some separation means permits separation of probe-coated microspheres bound to a complementary member of the pair from probe-coated microspheres not bound to a complementary member of the binding pair. This may include, for example, the methodologies employed in an agglutination type test or assay, in various well plate assays, utilizing dip sticks, magnetic separations, particle capture tests, and the like. In general, a complementary member of the binding pair is fixed to a surface, the probe bound to the microsphere containing incorporated electroactive markers allowed to incubate therewith in a suitable buffer, and complexed specific binding pair components separated from uncomplexed specific binding pair components.

FIG. 1 depicts one embodiment of the invention, in which carboxyl-modified microspheres (CME) containing an incorporated electroactive marker are coupled with a water soluble carbodiimide such as 1-ethyl-3-(3-dimethylaminopropyl) carbodiimide hydrochloride (EDAC) yielding an o-acylisourea intermediate. The resulting o-acylisourea intermediate microsphere is then incubated with a ligand, such as specific binding pair antibody member, that has an available amine. A microsphere with the ligand covalently bound by means of an amide bond results. It is to be understood that the embodiment of FIG. 1 is merely exemplary, and that any of a wide variety of linker technologies and techniques known in the art may be employed.

Figure 6:
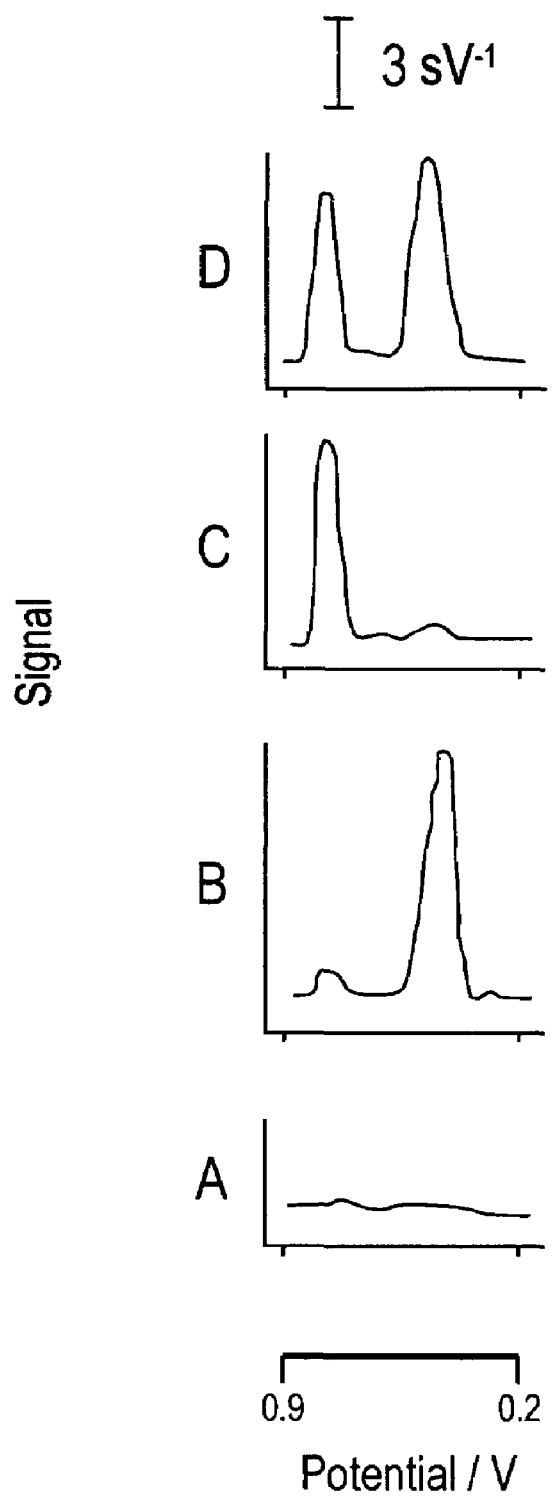
FIG. 6 is a plot of chronopotentiometric hybridization response to: (A) control, (B) 500 ng mL$^{-1}$ T1 (ferrocene), (C) 500 ng mL$^{-1}$ T2 (FCA), and (D) 500 ng mL$^{-1}$ T1 and T2.

Any given electroactive marker has a redox potential specific to such marker. For example, panel D of FIG. 6 shows two different peaks, representing two different electroactive markers, and FIG. 7 similarly shows two different electroactive markers at different concentrations. Different electroactive markers will produce peaks at different potentials, with generally a single peak specific to each electroactive marker, and thus different markers may readily be identified in a mixed solution. In general, up to at least six different electroactive markers can be detected in a mixed solution. It may readily be seen that multiple analytes or targets may be detected in a mixed target solution by use of electrochemically distinguishable electroactive markers. Thus, a plurality of sets of microspheres may be employed, with each set containing incorporated electroactive markers of a different redox potential, such that the different electroactive markers may be individually detected by electrochemical analysis. In this way, different analytes or targets may be detected. In some embodiments, different probes are employed, such as magnetic beads, polystyrene, or the like. In other embodiments, a first probe is conjugated to the microspheres with a first incorporated electroactive marker, a second probe is conjugated to the microspheres with a second incorporated electroactive marker, and so on, such that only a specific analyte or target binds thereto, with separation by any means, including use of a sandwich methodology, inhibition methodology or other means.

In one embodiment, the complementary member of the binding pair is bound to a substrate by means of one or more mechanisms described above. For example, the substrate may be a polystyrene well, dipstick, surface or the like. Following incubation, simple washing is used to remove uncomplexed microspheres with bound analyte.

In another embodiment, magnetic separation is employed. Use of microspheres, such as superparamagnetic particles made of iron oxide crystals dispersed in styrene or styrene/divinylbenzene monomers that are subsequently polymerized, is well known in the art. Such magnetic microspheres can be functionalized with any group, such as —COOH or —NH$_2$ groups, and may include one or more linkers, spacers or the like. In one embodiment a NeutrAvidin™ modified avidin (with removed carbohydrate and a lower isoelectric point) biotin-binding protein is conjugated to the surface of magnetic microspheres, and is employed to bind a biotinylated probe, such as DNA, antibody, antigen or the like.

Any form of magnetic particle may be employed in magnetic separation, including those disclosed in U.S. Pat. No. 6,368,800, relating to isolating biological target materials, particularly nucleic acids, such as DNA or RNA or hybrid molecules of DNA and RNA, from other substances in a medium using silica magnetic particles.

As set forth above, in the practice of the invention some means is employed to separate binding pair-complexed microspheres containing incorporated electroactive markers from similar microspheres without specific binding pair complexes, or with complexes below some threshold. It is also possible that different populations of binding pair-complexed microspheres are employed, with the microspheres of each population having an identifiably different incorporated electroactive marker, and further being associated with a different specific binding pair. Thus in a mixed pool of two or more populations of electrochemical beads, it is possible and contemplated that, for example, a different probe is associated with each population, and each population is separated based on the presence of a specific binding pair. The means of separation is not critical to the invention, so long as some means of separation is employed. Such separation methodologies are well known in the art. While the examples provided herein utilize magnetic separation, it is to be understood that a wide range of other methods can be employed. By way of example, it is possible to use separation methods such as qualitative agglutination, active agglutination, reverse passive latex agglutination, particle capture using an immunosorbent assay or immunosorbent test, centrifugation, centrifugal filtration, filtration, flow cytometry separation, and the like, all methods well known in the art.

Once the specific binding pair complexed microspheres, or populations of different specific binding pair complexed microspheres, containing incorporated electroactive markers have been separated, the electroactive markers are released from incorporation within the microsphere or from the surface of the microsphere. This may easily and conventionally be done by use of a solvent. For example, polymeric styrene or styrene-containing microspheres can be solubilized in solvents such as acetone, acetonitrile or the like. In general, solvents are known for all polymeric materials employed for microspheres, and selection of a solvent that does not interfere with electrochemical analysis is within the skill of an ordinary worker in the field.

Figure 3:
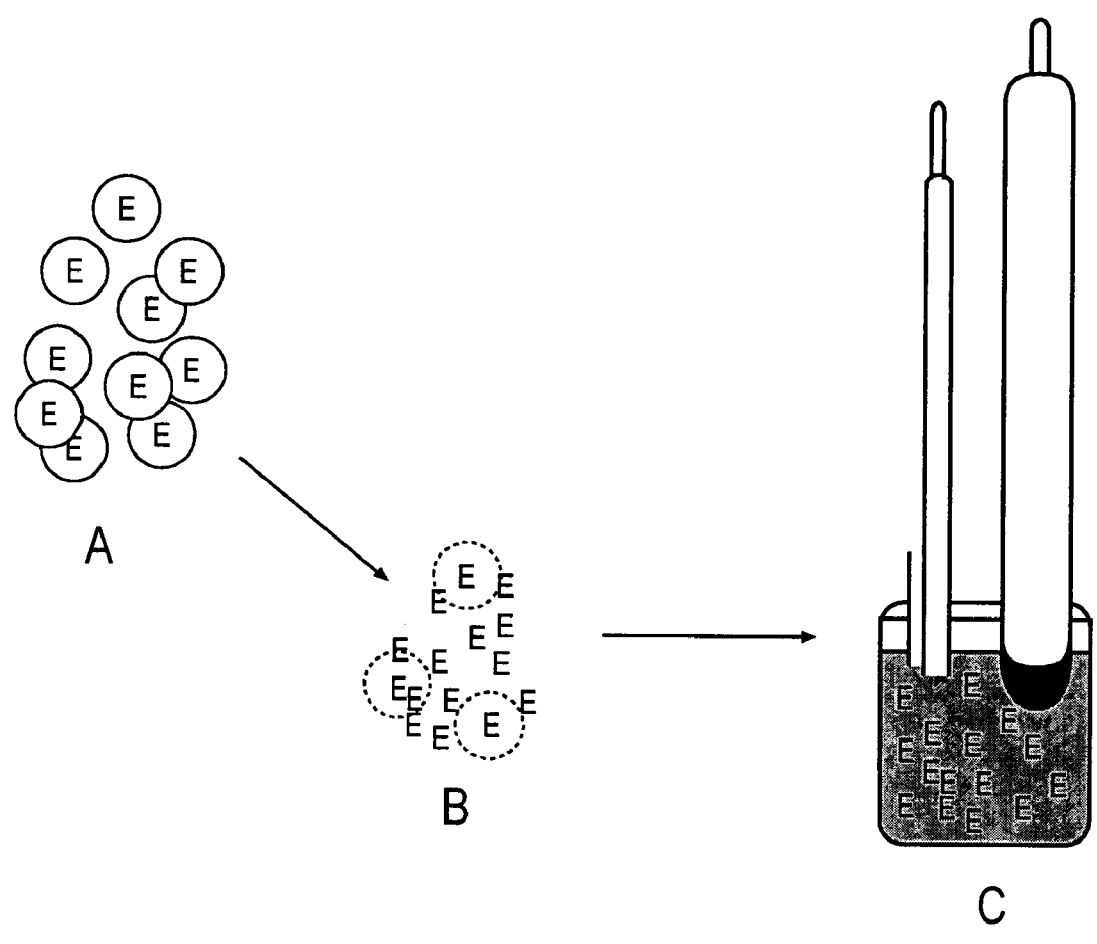
FIG. 3 is a schematic representation of an embodiment of the invention, wherein microspheres containing incorporated electroactive marker "E" undergo chemical treatment to release the marker E, with subsequent detection of Marker E by electrochemical detection.

Thus in one embodiment 10 to 100 μL of specific binding pair complexed microspheres, at a suitable concentration such as from about $10^5$ or $10^8$ particles/mL$^{-1}$, are added to a suitable solvent, such as 1 mL acetonitrile. Gentle stirring may be employed, and sufficient time is allowed to effect dissolution of the microspheres. The resulting solution contains the electroactive markers, and this solution is then subjected to electrochemical analysis. FIG. 3 graphically illustrates microspheres with incorporated electroactive marker "E" at step A, solubilization of the microspheres at step B (with solubilizing microspheres depicted by a dash-line circle), and subsequent electrochemical detection of the free electroactive marker E at step C.

The solvent may contain buffers, electrochemical adjuncts, and the like. In one embodiment employed with polystyrene-based microspheres, the solvent includes acetonitrile and 0.2 M tetraethylammonium-chloride.

In the practice of this invention, once the specific binding pair complexed microspheres have been separated, it is possible to permit a significant amount of time to pass before the microspheres are solubilized and/or the resulting solution analyzed by means of electrochemical analysis. Thus, detection and separation may occur at one site, with analysis at a distant or central location.

There are a variety of assay formats known to those of ordinary skill in the art for using a binding partner to detect a target or analyte in a sample. See, e.g., Harlow and Lane, *Antibodies: A Laboratory Manual*, Cold Spring Harbor Laboratory, 1988. In one embodiment, the assay involves the use of a first binding partner immobilized on microspheres containing an incorporated electroactive marker to bind to and remove target from the remainder of the sample. The bound target may then be detected and separated using a second binding partner. Suitable second binding partners include antibodies that bind to the binding partner/target complex. Such second binding partners may themselves be bound to a fixed substrate, such as a well or strip, to a magnetic microsphere, or to any other separation substrate. Alternatively, a competitive assay may be utilized.

In certain embodiments, a modified two-antibody sandwich assay may be employed. In one method, this assay may be performed by first contacting an antibody that has been immobilized on a microsphere with the sample, such that targets within the sample are allowed to bind to the immobilized antibody. Unbound sample is then removed from the immobilized target-antibody complexes. A second antibody is attached to a magnetic microsphere, a fixed support, or other separation means, which second antibody is capable of binding to a different site on the target. In other certain embodiments, a competitive inhibition type assay may be employed.

Once the antibody is immobilized on the microsphere as described above, the remaining protein binding sites on the microsphere are typically blocked. Any suitable blocking agent known to those of ordinary skill in the art, such as bovine serum albumin or Tween™ 20, may be used. The immobilized antibody and microsphere construct is then incubated with the sample, and target is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of target within a sample. Those of ordinary skill in the art will recognize that the time necessary to achieve equilibrium may be readily determined by assaying the level of binding that occurs over a period of time.

Unbound sample may then be removed by washing microspheres with an appropriate buffer, such as PBS containing 0.1% Tween™ 20. The second antibody, conjugated or bound to a magnetic microsphere, well, strip or other separation means, is then incubated with the immobilized antibody-target complex on the microsphere for an amount of time sufficient to detect the bound target. An appropriate amount of time may generally be determined by assaying the level of binding that occurs over a period of time. The separation means, which may be washing, agglutination, magnetic separation, centrifugal separation or other means, is then employed. Once the microspheres bound to the separation means by the sandwich, such as a two-antibody sandwich, have been separated, the microspheres may be solubilized, or the electroactive marker otherwise released, and the resulting solution containing the electroactive marker reporter subjected to electrochemical analysis.

Of course, numerous other assay protocols exist that are suitable for use with the microspheres containing incorporated electroactive markers of the present invention. The above descriptions are intended to be exemplary only.

It is possible and contemplated that the magnetic particles, such as iron-containing magnetic particles incorporated in a magnetic microsphere, may serve as the electroactive marker in the methods of the invention. In one embodiment, the magnetic microsphere has incorporated therein a super paramagnetic agent, such as magnetite, which may further serve as an electroactive marker. By way of example, a magnetic microsphere may be utilized in an assay system, and the captured magnetic microspheres dissolved, such as by an organic solvent, to release the incorporated iron oxide. The released iron can then be detected and quantified by cathodic stripping analysis, for example a negative-going differential-pulse voltammetric potential scan.

While release of the electroactive marker is most conveniently by use of a solvent, other methods of release can be employed. Thus, for example, temperature, pressure, enzymatic degradation and the like may be employed.

Specific examples of probe and target or analyte attachment to a substrate are provided herein, but are not intended to be limiting. Any means of attachment known in the art may be employed. Determination of relevant parameters, such as bond strength versus shear or other forces involved in the separation means, may be by conventional methodologies.

It should be understood that either member of a specific binding pair can constitute the target or analyte. For example, if circulating antigen is the target (as in PSA or cancer marker tests), then an antibody may be the probe. If antibody is the target (as in an HIV antibody test or other antibody titer test), then antigen may be the probe. It is further to be understood that "antigen" is employed in the broadest possible sense, such that for example, an anti-idiotype antibody may be an antigen, such that both the probe and target are antibodies.

Any of a variety of synthetic markers may be employed, such as molecules that bind antibodies, viral particles, prions and the like. In one embodiment, an amino acid construct can be employed as either the probe or target. Use of markers and compounds of this nature as probes or targets, and particularly as targets, is well known in the assay and immunochemical arts.

Further signal amplification utilizing the method of this invention may be obtained through the effect of the electroactive marker. For example, with a ferrocene-based electroactive marker, ferrocenyl ions accumulate at the surface of the working electrode, resulting in an ion exchange modified electrode.

Depending on the electroactive marker employed, it is also possible to add one or more reactants that result in signal amplification. For example, with iron oxide electroactive markers it is possible to add an oxidant, such as for example a bromate ion, to the detection system to effect catalytic regeneration of the iron (III) ions and an amplified stripping reduction current. Other methods and reagents for providing signal amplification are known in the electrochemical detection arts, and may similarly be employed with this invention.

The devices, systems and methods of this invention may be employed for any purpose for which specific binding pair assays are employed. Thus, application is found in industrial processes, environmental monitoring, biological separations, biological manufacturing, diagnosis or monitoring of infectious diseases, diagnosis or monitoring of other pathologies or conditions (e.g., pregnancy, occult blood, myoglobin, fibrin degradation products), plant health and other agronomy applications, veterinary medicine, law enforcement, food safety and the like.

Microspheres with incorporated electroactive markers have particular utility for DNA analysis. The amplification strategy relies on the use of microspheres which have internally incorporated electroactive markers, preferably water-insoluble electroactive markers, in a manner analogous to the entrapment of fluorescent agents in commercial fluorescent-entrapped microspheres. The resulting electroactive microspheres are capable of carrying a huge number of marker molecules and hence offer a dramatic amplification of single hybridization events and remarkably low detection limits (down to at least $5.1 \times 10^{-21}$ mol or ~31,000 molecules). Approximately $5 \times 10^{11}$ molecules of the ferrocenecarboxaldehyde (FCA) marker have thus been incorporated in a single microsphere. The huge signal amplification is coupled to effective discrimination against non-complementary nucleic acids; for example, discrimination against a huge excess ($10^7$) of non-complementary nucleic acids. Such microspheres may further be employed for multi-target detection, such as with groups of microspheres with different probes and with different incorporated electroactive markers, and for enhancing the sensitivity of other bioassays.

INDUSTRIAL APPLICABILITY

The invention is further illustrated by the following non-limiting examples.

EXAMPLE 1

Apparatus for Electrochemical Detection.

Chronopotentiometric measurements were performed with a potentiometric stripping unit PSU20 (Radiometer) controlled by TAP2 software (Radiometer). The preparation of the probe-coated magnetic microspheres and the hybridization reaction were performed on a MCB 1200 Biomagnetic Processing Platform (Dexter Corporation Magnetic Technologies, Fremont, Calif.). An IEC Micromax centrifuge (OM3590) and a Vortex Genie2 shaker were used during ferrocene or FCA incorporated microsphere labeling of target DNA.

EXAMPLE 2

Preparation of Probe-Coated Magnetic Microspheres

The probe immobilization onto the magnetic microspheres was performed with a MCB 1200 Biomagnetic Processing Platform. 50 µg of ~0.8 µm diameter streptavidin-coated magnetic microspheres (Bangs Laboratories) were transferred into a 1.5 mL centrifuge tube. The microspheres were washed with 100 µL TTL buffer (100 mM Tris-HCl, pH 8.0, and 0.1% Tween™ 20, 1 M LiCl) and resuspended in 20 µL TTL buffer. Subsequently, 4.0 µg of the biotinylated probe were added and incubated for 15 minutes at room temperature with gentle mixing. The coated microspheres were then separated, and washed twice with 100 µL TT buffer (250 mM Tris-HCl, pH 8.0, and 0.1% Tween™ 20) and resuspended in 20 µL hybridization buffer (750 mM NaCl, 150 mM sodium citrate).

EXAMPLE 3

Preparation of Electroactive Microspheres.

Electroactive microspheres were made by taking dry polystyrene co-polymeric microspheres and swelling the microspheres in an organic solvent, such as propanol, containing either ferrocene or ferrocenecarboxaldehyde (FCA). In one embodiment, 95% propanol (v/v) was employed with 5% ferrocene or FCA in chloroform. After incubation for a period of time sufficient to permit introduction of the FCA into the swollen matrix of the microspheres, yet short enough to not permit permanent microsphere aggregations, a second solvent, such as heptane, was added that resulted in reduction in size of the microspheres. Alternatively, evaporation of the solvent is employed. The resulting electroactive microspheres were washed, preferably in solvent such as heptane, activated with a chemical linker, and covalently bonded to NeutrAvidin™. The NeutrAvidin™-coated electroactive microspheres were stored until used. Other solvent systems for swelling the microspheres are known in the art and may be employed in incorporating electroactive markers. Similarly, a variety of methods, including use of various second solvent systems, are known for removing the first solvent, and may similarly be employed.

EXAMPLE 4

Labeling the Target DNA with the Electroactive Microspheres.

The appropriate amount of the biotinylated target (or non-complementary) nucleic acid was added to 50 µL NeutrAvidin™-coated electroactive microspheres of Example 3 (usually at $18.73 \times 10^6$ particles mL$^{-1}$) in TTL buffer and incubated for 30 minutes with gentle mixing, washed with 100 µL TT buffer, centrifuged at 8000 rpm for 2 minutes and resuspended in 30 µL hybridization solution.

EXAMPLE 5

Hybridization and Detection.

The hybridization event proceeded by gently mixing solutions containing the probe-coated magnetic microsphere of Example 2 and the target-coated electroactive microspheres of Example 4 for 20 minutes. This was followed by washing twice with 90 µL TT buffer and resuspension in 20 µL TT buffer. The resulting 20 µL sample of electroactive microsphere and magnetic microsphere specific binding pair complexes was then spiked into a 1 mL acetonitrile (containing 0.2 M tetraethylammonium chloride) dissolution/detection solution, where the spheres were dissolved for 5 minutes under gentle stirring. Chronopotentiometric detection of the released FCA was carried out using the apparatus of Example 1 at a glassy carbon electrode (polished with a 0.05 µm aluminum slurry) using a constant current of +2 µA (following 5 seconds at +0.20 V), utilizing Ag/AgCl and platinum wire reference and counter electrodes.

EXAMPLE 6

Protocol Summary.

Figure 2:
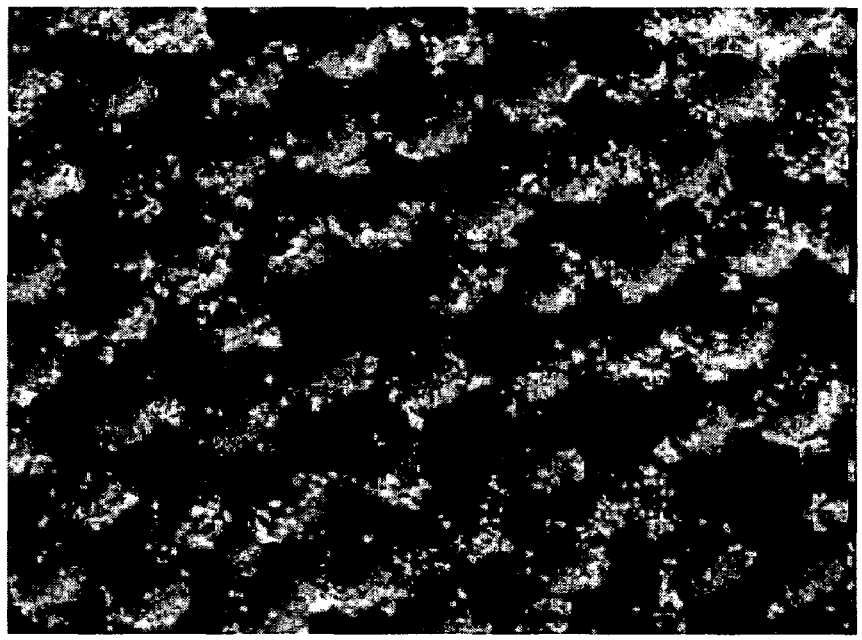
FIG. 2 is a scanning electron micrograph of DNA-particle assembly produced following a 20 minute hybridization with 40 mg L$^{-1}$ target, using 10 µm microspheres with bound target and 0.8 µm magnetic spheres with bound probe, taken on a Hitachi S3200 instrument.

DNA probe-coated magnetic microspheres of Example 2 were introduced to a 50 µL hybridization solution along with the complementary DNA-coated FCA electroactive microspheres of Example 4. Following a 20 minute hybridization and magnetic separation, the resulting magnetic microspheres/DNA/FCA electroactive microsphere conjugates were transferred into an acetonitrile solution, where the microspheres were dissolved with concurrent release of the FCA molecules. This was followed by chronopotentiometric detection of the released marker at a glassy-carbon transducer. FIG. 2 shows a scanning electron micrograph of the DNA-linked particle assembly which resulted from the hybridization event. This image indicates that 10 μm electroactive microspheres are cross-linked to the smaller (~0.8 μm) magnetic microspheres through the DNA hybrid. Such hybridization-induced aggregation is consonant with other particle-based DNA assays. The image indicates also that the integrity of the particle-linked DNA network is maintained during the washing and magnetic-separation steps. Similar particle-linked DNA networks were observed using electroactive microspheres of 5 and 20 μm diameters. In contrast, such aggregation was not observed in the presence of non-complementary DNA, and a 2-bp mismatched DNA resulted in greatly smaller aggregates.

EXAMPLE 7

Breast Cancer Gene Detection.

Figure 4:
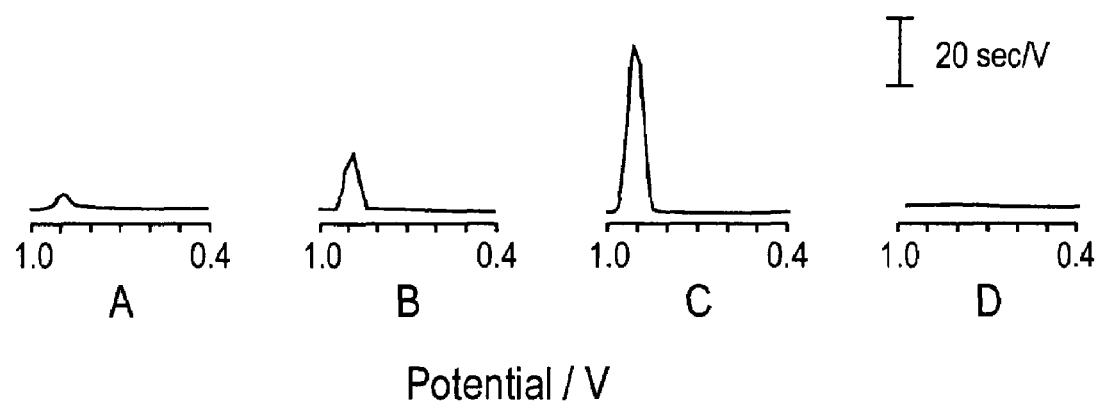
FIG. 4 provides plots of chronopotentiometric hybridization signals for 0.01 (A), 0.1 (B), 100 (C) ng L$^{-1}$ (ppt) DNA target and 500 µg L$^{-1}$ (ppb) non-complementary DNA (D). Hybridization time, 20 minutes in 0.75 M NaCl/0.15 M sodium citrate; marker release time, 5 minutes; constant current, 2 µA. The oligonucleotides (acquired from Sigma-Genosys Ltd.) had the following sequences: probe: 5'-biotin-GTA TTA GCT TTT CTT GAT AAA ATC CTC A (SEQ ID NO: 1); target: 5'-biotin-GTA TTA GCT TGA GGA TTT TAT CAA GAA A (SEQ ID NO: 2); non-complementary: 5'-biotin-GTA TTA GCT GAA CAA AAG GAA GAA AAT C (SEQ ID NO: 3). Measurements were carried out with a Trace Lab PSU20 system (Radiometer), controlled by the TAP2 software in a 1.0 mL cell containing acetonitrile/0.2M tetraethylammonium-chloride solution.

Electrical detection of DNA segments related to the BRCA1 breast cancer gene was used for illustrating the enhanced signal per hybridization reaction. FIG. 4 displays typical chronopotentiograms for extremely low target concentrations (0.01 to 10,000 ng $L^{-1}$; A-C), along with the corresponding response for a huge (~$10^3$–$10^7$ fold) excess of a non-complementary nucleic acid (D). Well-defined oxidation peaks were observed for the low target levels ($E_p$=+0.88 V). The favorable response of the 10 pg $L^{-1}$ DNA target (A) indicates a remarkably low detection limit of 1 pg $L^{-1}$ ($10^{-16}$M) with a 20 minute hybridization time. This detection limit corresponds to $5.1 \times 10^{-21}$ mol (i.e., ~31,000 molecules) in the 50 μL sample, and represents the lowest value reported for electrical DNA detection. The detection system is $10^6$ and $10^3$ times more sensitive than analogous DNA sensing based on ferrocene-conjugated oligonucleotides, or the most sensitive (liposome-amplified) DNA electrical sensing. The remarkable sensitivity is coupled to minimal contributions from nonhybridized DNA. A negligible signal is observed for the 500 μg $L^{-1}$ non-complementary DNA (D). Apparently, the combination of effective magnetic separation and an organic detection medium eliminates non-specific adsorption effects. A 1,000 ng $L^{-1}$ 2-bp mismatch solution yielded a small response, corresponding to that of a 0.1 ng $L^{-1}$ target.

EXAMPLE 8

Calibration Analysis.

Figure 4A:
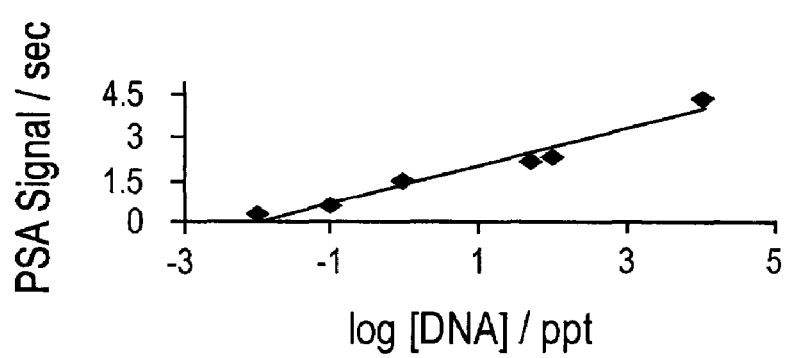
FIG. 4A is a calibration plot for DNA target concentrations ranging from 0.01 to 10,000 ng L$^{-1}$ of the reactants of FIG. 4.

The target measurements of Example 7 were utilized in 6-point calibration experiments over the 0.01–10,000 pg $L^{-1}$ range. The peak area increased nonlinearly with the target concentration. Yet, the resulting logarithmic plot, as shown in FIG. 4A is linear over the entire range and is suitable for quantitative work. Saturation of the probe hybridization sites and changes in the degree of aggregation account for the nonlinear concentration dependence. The amplified signal is coupled to a relatively good reproducibility (e.g., a RSD of 23% for 5 successive measurements of 100 pg $L^{-1}$). Such signal variations relate primarily to reproducibility of the aggregation process.

EXAMPLE 9

Dual Electroactive Marker Microspheres for DNA Detection.

Electroactive microspheres with either incorporated FCA or ferrocene were prepared as in Example 3. The magnetic microspheres had a binding capacity of 1.13 μg biotin-FITC/mg magnetic microspheres, while the FCA incorporated microspheres had a binding capacity of 0.009 μg biotin-FITC/mg microsphere and the ferrocene incorporated microsphere had a binding capacity of 0.006 μg biotin-FITC/mg microsphere. Probe immobilization onto magnetic microspheres was performed with a MCB 1200 Biomagnetic Processing Platform, with 50 μg of streptavidin-coated microspheres transferred into a 1.5 mL centrifuge tube. The magnetic microspheres were washed with 100 μL TTL buffer (100 mM Tris-HCl, pH 8.0, and 0.1% Tween™ 20, 1 M LiCl) and resuspended in 20 μL TTL buffer. Subsequently, 4.0 μg of the biotinylated probe (P1 or P2) was added and incubated for 15 minutes at room temperature with gentle mixing. The coated magnetic microspheres were then separated, and washed twice with 100 μL TT buffer (250 mM Tris-HCl, pH 8.0, and 0.1% Tween™ 20) and resuspended in 20 μL hybridization buffer (750 mM NaCl, 150 mM sodium citrate). The appropriate amount of the biotinylated-probe nucleic acid (P3 or P4) was added to the appropriate amount of neutravidin-coated electroactive marker microspheres (18.73×$10^6$ particles $mL^{-1}$) in TTL buffer and incubated for 30 minutes with gentle mixing, washed with 100 μL TT buffer, and centrifuged at 8000 rpm for 2 minutes. The hybridization event proceeded by adding the appropriate amount of target nucleic acid (T1 or T2) and the electroactive marker incorporated microsphere solutions (P3 and P4) (50 μL total volume, hybridization solution) with gentle mixing for 20 minutes, followed by adding 10 μL each of the magnetic microsphere probe solutions (P1 and P2) and mixing for an additional 20 minutes. This was followed by washing three times with 90 μL TT buffer and resuspending the conjugate in 20 μL TT buffer. The resulting 20 μL sample was then spiked into a 1 mL acetonitrile (containing 0.2M tetraethylammonium chloride) dissolution/detection solution. Chronopotentiometric detection of the released marker(s) was carried out at a glassy carbon electrode (polished with a 0.05 μm alumina slurry) using a constant current of +2 μA (following 5 seconds at +0.20V), using Ag/AgCl reference and platinum-wire counter electrodes. All oligonucleotides were purchased from Life Technologies (Grand Island, N.Y.) and had the following sequences:

P1:  (SEQ ID NO: 4)
5'-GGGTTTATGAAAAACACTTT-biotin

P2:  (SEQ ID NO: 5)
5'-ACACTGGGTGGGCTAGGGAA-biotin

P3:  (SEQ ID NO: 6)
5'-biotin-GACCTAGTCCTTCCAACAGC

P4:  (SEQ ID NO: 7)
5'-biotmn-CAAAACGTATTTTGTACAAT

T1:  (SEQ ID NO: 8)
5'-AAAGTGTTTTTCATAAACCCATTATCCAGGACTGTTTATAGCT-GTTGGAAGGACTAGGTC

T2:-  (SEQ ID NO: 9)
5'-TTCCCTAGCCCACCCAGTGTGCAAGGGCAGTGAAGACTT-GATTGTACAAAATACGTTTTG

Figure 5:
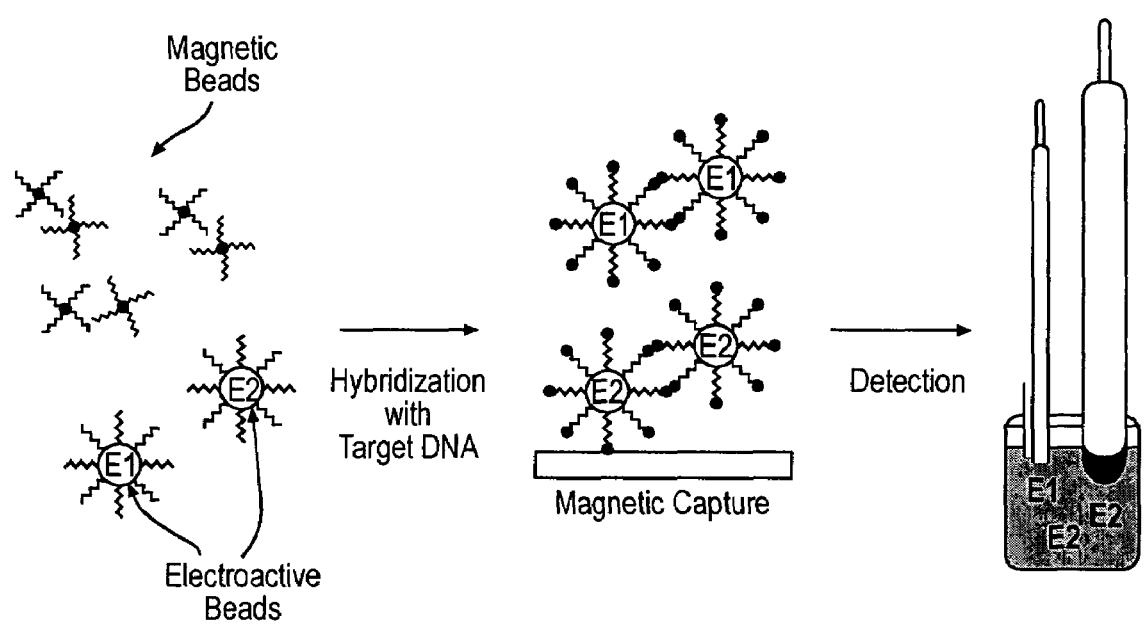
FIG. 5 is a schematic depicting dual electroactive markers, wherein is shown introduction of probe-coated magnetic microspheres and probe-labeled electroactive marker encapsulated microspheres, hybridization with target DNA and magnetic separation, and dissolution of the spheres in acetonitrile, release of the marker and its chronopotentiometric detection at a glassy carbon electrode.

The scheme for the dual electroactive microsphere DNA detection protocol is shown in FIG. 5. Probe-coated magnetic microspheres and target-coated electroactive microspheres (containing electroactive markers E1 and separately E2) were mixed with appropriate amounts of target DNA and after hybridization, magnetic separation, and transfer to the dissolution/detection solution the released marker is detected at a glassy carbon transducer using chronopotentiometric stripping analysis. Thus the protocol combines the advantages of magnetic separation for isolating the DNA duplex, multiplexing capabilities by taking advantage of different ferrocene compounds, and signal amplification from target-loaded electroactive microspheres. The two marker molecules, FCA and ferrocene, exhibited well resolved peak potentials at +0.55 and 0.88 V respectively, although the prepared FCA microspheres exhibited higher sensitivity than the ferrocene microspheres, such that the amount of electroactive microspheres used in the labeling step was adjusted to achieve similar sensitivities for the two electroactive markers.

FIG. 6 depicts the response of the dual-label bioassay in response to 500 ppb of the DNA targets with the FCA and ferrocene electroactive markers respectively (D); 500 ppb T1 (C); 500 ppb T2 (B); and a control sample (A).

Figure 7:
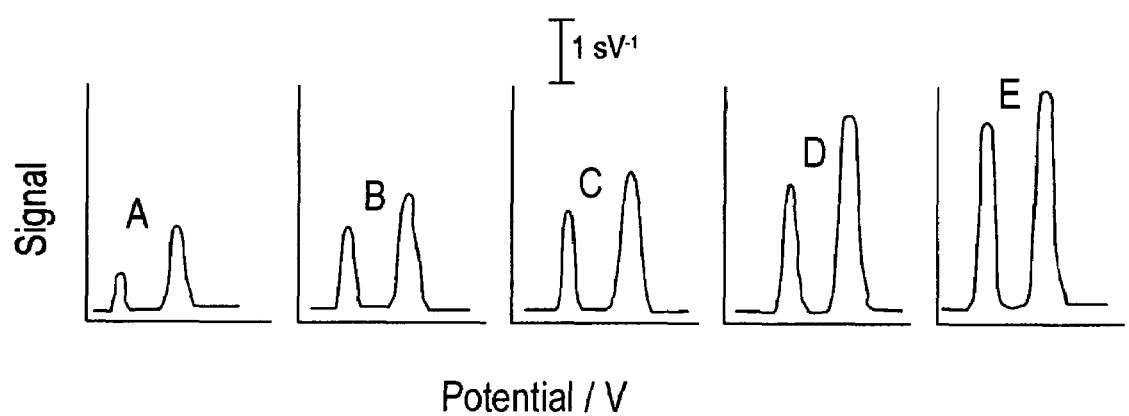
FIG. 7 is a plot of chronopotentiometric signals for (A) 250, (B) 500, (C) 750, (D) 1000 and (E) 1250 ng mL$^{-1}$ T1 and T2, utilizing 10 μL magnetic beads, 20 μL FCA electroactive microspheres, and 40 μL ferrocene electroactive microspheres.

The position and size of the product peaks provide the desired identification and quantitative information, respectively, on a given target DNA. Dual target quantitation is illustrated in FIG. 7 from the chronopotentiometric response to sample mixtures containing increasing levels of the two target oligonucleotides: 250 (A), 500 (B), 750 (C), 1000 (D), and 1250 ppb (E). Well-defined and resolved peaks were observed, with peaks proportional to the concentration of corresponding DNA targets, indicating minimal cross interference and absence of surface fouling of the glassy carbon electrode.

EXAMPLE 10

Preparation of Nanoparticles Electroactive Markers.

Electroactive cadmium sulfide, lead sulfide, and zinc sulfide nanoparticles were prepared by taking 50 mL aliquots of $10^{-4}$ M aqueous $CdCl_2$, $ZnCl_2$, or $PbCl_2$ solutions (pH 5.8) and 50 mL of a 5 nM octadecanethiol (ODT) solution (prepared in petroleum ether) mixed into a conical flask; the resulting biphasic mixture was shaken vigorously. Hydrogen sulfide (prepared by mixing ZnS and HCl) was then bubbled through the stirred mixture for 20 minutes, during which the solutions became yellow (CdS), white (ZnS), or black (PbS); the stirring was then stopped, and the nanoparticles were collected in the petroleum ether organic phase. The nanoparticles/petroleum ether solution was rotary evacuated leading to a colored powder (yellow, white, or black depending on the specific sulfide). This powder was washed with ethanol to remove the excess ODT molecules. Subsequently, the powders were dispersed in chloroform.

EXAMPLE 11

Incorporation of Nanoparticle Electroactive Markers in Microspheres.

Polystyrene-based microspheres were dried under vacuum. A selected nanoparticle of Example 10, dispersed in chloroform, was mixed with propanol (95.0% v/v propanol, 5.0% v/v nanoparticles in chloroform). Subsequently, the dried polystyrene-based microspheres were added to the mixture. The incorporation process proceeded by shaking the resulting mixture for 30 minutes at room temperature. The microspheres were then dried under vacuum. Heptane was added to the dried microspheres, and the mixture was stirred for 50 minutes at room temperature followed by solvent decantation. The washing process was repeated until discrete microspheres were obtained. Finally, the electroactive marker incorporated microspheres were dried under vacuum.

EXAMPLE 12

Surface Associated Gold Nanoparticle Incorporated Microspheres.

20 μg of streptavidin-coated polystyrene microspheres were mixed with a target oliognucleotide to a final volume of 25 μL in TTL buffer. Following incubation and centrifugation, 4 μL of albumin-biotin labeled 5 nm colloidal gold (Sigma), containing about $10^{11}$ nanoparticles, was added to the microspheres in a vial containing 21 μL TTL buffer. After washing, the targeted-labeled and gold-surface loaded microspheres were suspended into 50 μL of TTL buffer as a hybridization buffer together with probe-functionalized magnetic microspheres. After incubation for requisite time to permit hybridization, the resulting DNA-linked specific binding pairs including the gold-surface loaded microspheres were washed, separated, and suspended in a gold dissolution and detection medium consisting of 1 M HBr and 1 mM $Br_2$. In an alternative protocol, following incubation to permit hybridization, the resulting DNA-linked specific binding pairs including the gold-surface loaded microspheres were washed with water, followed by the addition of 25 μL of GoldEnhance (Nanoprobe, Inc., Yaphank, N.Y.), a gold enhancer solution providing catalytic deposition of gold ions on nanoparticles. After catalytic gold precipitation onto the gold nanoparticles bound to the surface of the polystyrene-based microspheres, the microspheres were washed and suspended in a gold dissolution and detection medium consisting of 1 M HBr and 1 mM $Br_2$. In both instances, following dissolution of the gold tag chronopotentiometric stripping measurements were performed using screen-printed carbon ink working electrodes and silver-silver chloride reference electrodes, with pretreated of the electrode surface at +1.2 V for three minutes, with a two minute deposition at −0.8 V using a stirred 1 M HBr and 1 mM $Br_2$ solution, with subsequent stripping using an applied anodic current of +5 μA.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of analyzing a sample for the presence of a member of a specific binding pair, the method comprising:
   providing a polymeric microsphere having an electroactive molecule encapsulated within the polymeric microsphere and a first member of a specific binding pair attached to the polymeric microsphere wherein the polymeric microsphere is not a liposome;
   introducing a sample suspected to comprise a second element of the specific binding pair complex to the polymeric miscrosphere;
   selecting for the polymeric microsphere by formation of a specific binding pair complex in fluid suspension;
   releasing the electroactive molecule from the polymeric microsphere with an organic solvent; and
   detecting the specific binding pair complex via voltammetry or amperometry for the electroactive molecule released from the polymeric microsphere.

2. The method of claim 1 wherein tile polymeric microsphere is insoluble in an aqueous solution.

3. The method of claim 2 wherein the polymeric microsphere is a polystyrene-based microsphere.

4. The method of claim 1, wherein the providing steP comprises incubating the polymeric microsphere in an organic solvent including the electroactive molecule.

5. The method of claim 1 wherein the selecting step comprises binding of the first member of the specific binding pair attached to the polymeric microsphere and a second member of the specific binding pair attached to a substrate.

6. The method of claim 5 wherein the first member of the specific binding pair attached to the polymeric microsphere comprises a covalent bond with a functional group on the surface of the microsphere.

7. The method of claim 5 wherein the substrate comprises a magnetic particle.

8. The method of claim 1 wherein the selecting step comprises incubating.

9. The method of claim 1 wherein the specific binding pair complex comprises a pair selected from the group consisting of an antigen/antibody, enzyme/substrate, oligonucleotide/DNA, chelator/metal, enzyme/inhibitor, bacteria/receptor, virus/receptor, hormone/receptor, DNA/RNA, RNA/RNA, and an oligonucleotide/RNA complex.

10. The method of claim 1 wherein the releasing step comprises solubilizing the polymeric microsphere.

11. The method of claim 1 wherein the electroactive molecule comprises a metallocene.

12. The method of claim 1 wherein the electroactive molecule comprises a nanoparticle.

13. The method of claim 1 wherein the electroactive molecule comprises a metal.

14. A method of analyzing a sample for the presence of two or more analytes, the method comprising:
   providing a first polymeric micro sphere having a first electroactive molecule incorporated into a body of the first polymeric microsphere;
   providing a second polymeric microsphere having a second electroactive molecule electrochemically distinguishable from the first electroactive molecule encapsulated within the body of the second polymeric microsphere wherein neither the first polymeric microsphere nor the second polymeric micropshere is a liposome;
   attaching a first binding pair member specific to a first analyte to the first polymeric microsphere;
   attaching a second binding pair member specific to a second analyte to the second polymeric microsphere;
   incubating the first polymeric microsphere and second polymeric microsphere in a solution comprising the sample to be analyzed;

selecting for the first polymeric microsphere and second polymeric microsphere by formation of specific binding pair complexes in fluid suspension; and releasing the electroactive molecules from the first and second polymeric microspheres with an organic solvent detecting the specific binding pair via voltammetry or amperometry for the first electroactive molecule and the second electroactive molecule released from the first polymeric microsphere and the second polymeric microsphere.

15. The method of claim 14 wherein at least one of the first or second polymeric microsphere is insoluble in an aqueous solution.

16. The method of claim 15 wherein at least one of the first or second polymeric microsphere is a polystyrene-based microsphere.

17. The method of claim 14 wherein the attaching step comprises forming a covalent bond with a functional group on a surface of the polymeric microsphere.

18. The method of claim 14 wherein the specific binding pair complex is selected from the group consisting of an antigen/antibody, enzyme/substrate, oligonucleotide/DNA, chelator/metal, enzyme/inhibitor, bacteria/receptor, virus/receptor, hormone/receptor, DNA/RNA, RNA/RNA, and an oligonucleotide/RNA complex.

19. The method of claim 14 further comprising the step of releasing the first electroactive molecule from the first polymeric microsphere and the second electroactive molecule from the second polymeric microsphere.

20. The method of claim 19 wherein the releasing step comprises solubilizing the first polymeric microsphere and the second polymeric microsphere.

21. The method of claim 14 wherein the first electroactive molecule and the second electroactive molecule comprise metallocenes.

22. The method of claim 14 wherein the first electroactive molecule and the second electroactive molecule comprise nanoparticles.

23. The method of claim 14 wherein the first electroactive molecule and the second electroactive molecule comprise metal.

* * * * *